United States Patent [19]

Gauri

[11] 4,067,877
[45] Jan. 10, 1978

[54] ω-SUBSTITUTED ALKANES AND 1-HYDROXYALKANES

[75] Inventor: Kailash Kumar Gauri, Lentfoehrden, Germany

[73] Assignee: Robugen GmbH, Germany

[21] Appl. No.: 640,961

[22] Filed: Dec. 15, 1975

Related U.S. Application Data

[63] Continuation of Ser. No. 368,597, June 11, 1973, abandoned.

[51] Int. Cl.² .................. C07D 213/46; C07D 213/52
[52] U.S. Cl. ................................ 260/297 Z; 424/251; 424/263; 260/251 R; 260/294.8 R
[58] Field of Search ..................... 260/297 Z, 294.8 R

[56] References Cited

PUBLICATIONS

Gauri et al., Documenta Ophthalmogica Proceeding Series, Xth I.S.C.E.R.G. Symposium, Los Angeles, Ca., Aug. 20-23, 1972, pp. 119 to 123.
Mikhailov et al., Izv. Akad. Nauk SSSR, vol. 11, pp. 2588-2591 (1974).
Knunjanz, Ber Deut. Chem. vol. 68, pp. 397 to 399 (1935).
Shepherd, et al., J. Am. Chem. Soc. vol. 64, pp. 2532 to 2537 (1942).
Chauvelier, Bull. Soc. Chim France 1954, pp. 734 to 739.
Sharp, J. Chem. Soc. 1939, pp. 1855 to 1857.
Rath, Annalen der Chemie, vol. 484, pp. 52-64 (1930).
Binz et al., Annalen der Chemie, vol. 489, pp. 107-118 (1931).
Decker et al., Chemical Abstracts, vol. 6, pp. 225 to 227.

Primary Examiner—John D. Randolph
Attorney, Agent, or Firm—Birch, Stewart, Kolasch and Birch

[57] ABSTRACT

Straight- and branched-chain alkanes and 1-hydroxyalkanes of 4 to 18 carbon atoms, substituted in the ω-position by hetero-cyclic groups having the formula:

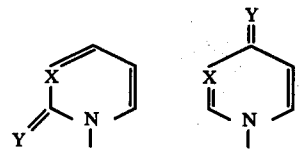

wherein X is a methine group or a nitrogen atom and Y is oxygen or sulfur are prepared by reacting a haloalkane or a haloalkanol with an alkali metal salt of a compound containing the desired heterocyclic group, such as a pyridone or a substituted pyrimidine. The compounds have been found to be useful in accelerating the dark adaptation, as determined in tests with mice.

2 Claims, 2 Drawing Figures

ω-SUBSTITUTED ALKANES AND 1-HYDROXYALKANES

This application is a continuation of copending application Ser. No. 368,597, filed on June 11, 1973, now abandoned.

The present invention relates to straight or branched-chain alkanes and 1-hydroxyalkanes of 4 to 18 carbon atoms, substituted in the ω-position by heterocyclic residues of the following general formula:

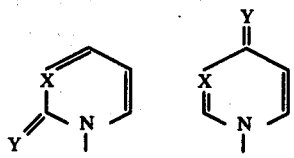

wherein X is a methine group or a nitrogen atom and Y is an oxygen atom or a sulfur atom, and to a process for preparing said compounds.

One of the objects of the present invention is to provide novel compounds having useful pharmaceutical properties.

Another object of the invention is to provide a relatively simple and effective process for preparing these compounds in a high yield.

These and other objects and advantages of the present invention will become apparent to those skilled in the art from a consideration of the present specification and claims, taken in conjunction with the accompanying drawings.

Figure 1:
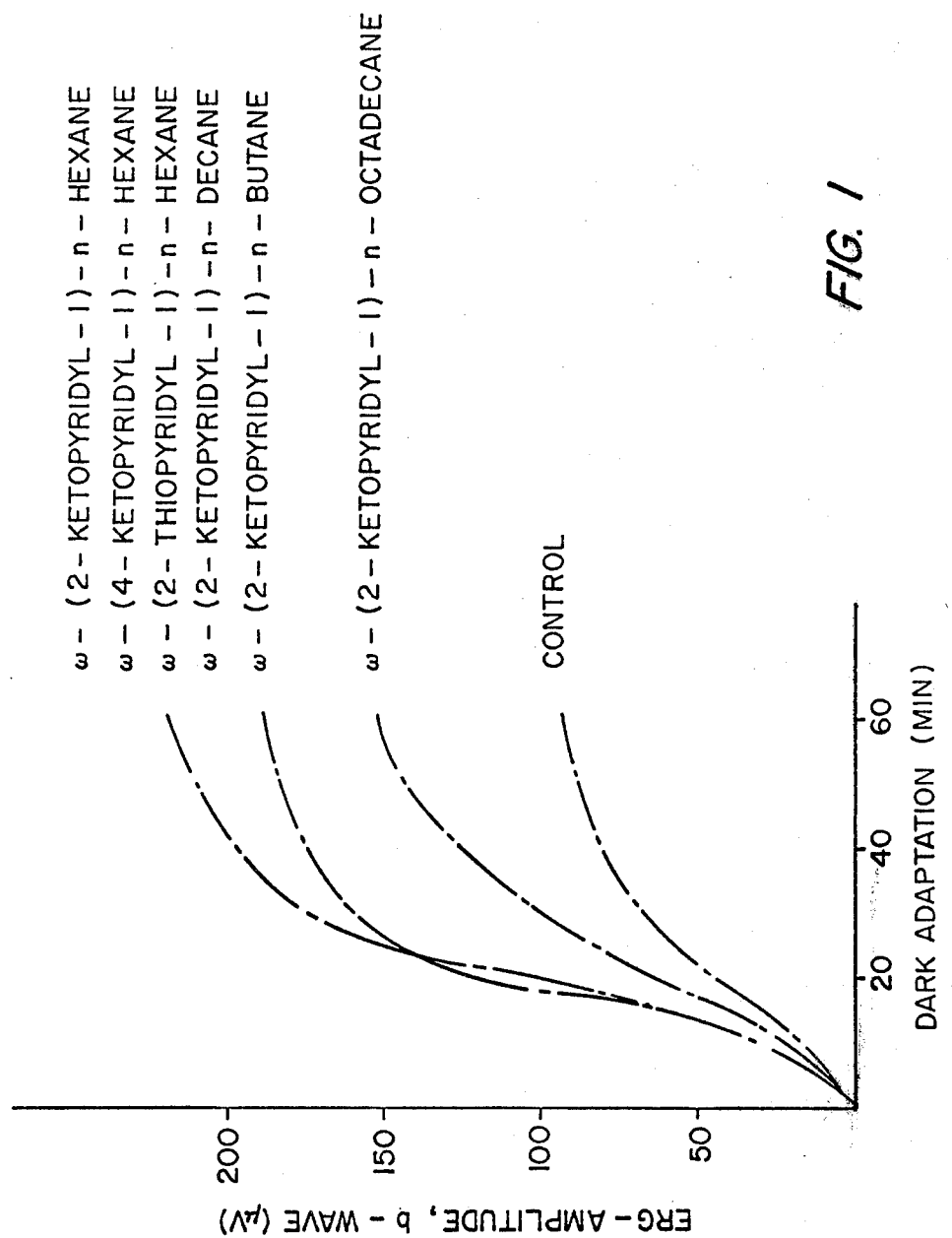
Figure 2:
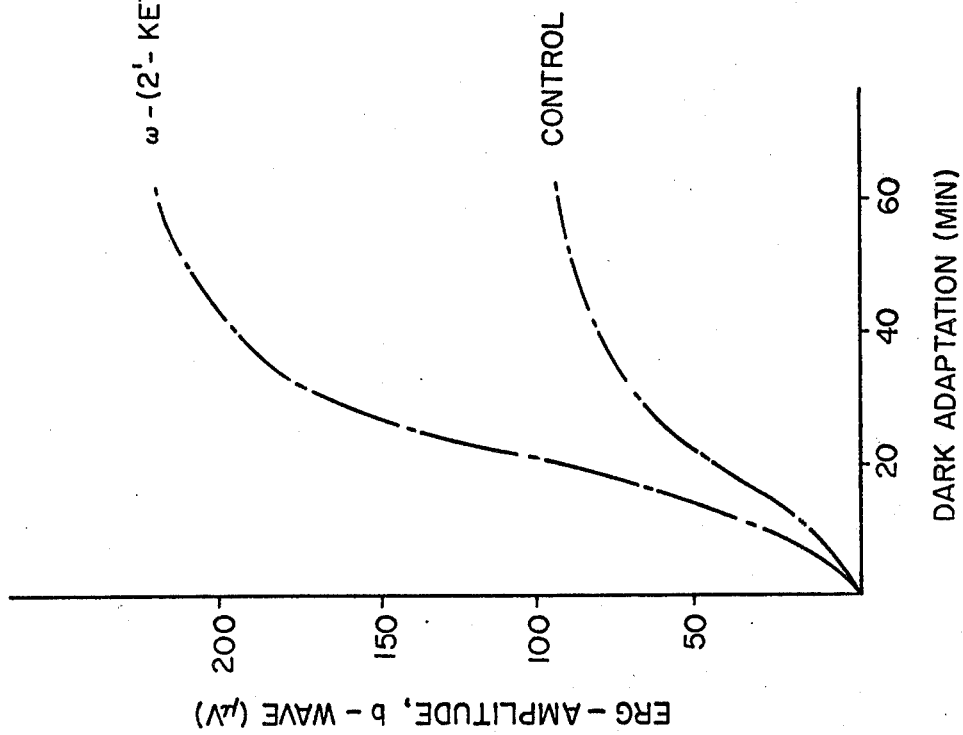

The compounds of the invention possess the special property of accelerating the dark adaptation. This conclusion is based upon tests conducted in animals, particularly mice, as carried out in accordance with conventional techniques therefor. This effect was determined on the basis of investigations carried out by means of an electroretinogram. The results obtained are illustrated in FIGS. 1 and 2 of the appended drawings.

The compounds of the present invention are prepared in accordance with the mode of operation set forth in the following Examples. These Examples are given merely as illustrative of the present invention and are not to be considered as limiting. Basically, the compounds are prepared by reacting a haloalkane or a haloalkanol with an alkali metal salt of a compound containing the above-described heterocyclic group, for example, 2-pyridone, γ-pyridone, a halo-substituted pyridone, or a keto- or halo-substituted pyrimidine.

EXAMPLE 1

ω-(2-Ketopyridyl-1)-n-hexane 17 g. of 1-bromohexane and 13 g. of pyridone-2 potassium salt are refluxed in 50 ml. of ethanol for 2 hours under agitation. The thus-formed potassium bromide is filtered off, the filtrate is concentrated under vacuum, and it is thereafter fractionated under vacuum by a water-jet aspirator. The ω-(2-ketopyridyl-1)-n-hexane passes over at about 160° C.

Yield: almost quantitative

Analysis: $C_{11}H_{17}ON$: Molecular weight: 179: Calculated: C, 73.7; H, 9.5; N, 7.8. Found: C, 73.5; H, 9.6; N, 7.9.

EXAMPLE 2

ω-(2-Thiopyridyl-1)-n-hexane 17.9 g. of ω-(2-ketopyridyl-1)-n-hexane is dissolved in 150 ml. of "Decalin" [decahydronaphthalene] and reacted under heating with 24 g. of phosphorus pentasulfide for about 3 hours. After cooling, the "Decalin" is removed by decanting, and the residue is taken up in 2N NaOH and extracted with chloroform. The chloroform solution is dried over sodium sulfate, concentrated under vacuum, and fractionated by means of an oil pump. The desired reaction product passes over at 160° C.

Yield: 17 g. ≈ 80% of theory.

Analysis: $C_{11}H_{17}NS$: Molecular weight: 195.3: Calculated: C, 67.65; H, 8.76; N, 7.17; S, 16.41. Found: C, 67.78; H, 8.65; N, 7.22; S, 16.35.

EXAMPLE 3

ω-(5-Chloro-2-ketopyridyl-1)-n-hexane

This substance is obtained in an 85% yield by employing the 5-chloropyridone-2 potassium salt as a starting material in the process of Example 1. By fractionation with an oil pump, the desired reaction product passes over at 132° C.

EXAMPLE 4

ω-(4-Ketopyridyl-1)-n-hexane 17 g. of hexyl bromide and 9.5 g. of γ-pyridone are heated under reflux in a solution of 2.6 g. of Na in 150 ml. of ethanol for about 1 hour and then evaporated to dryness. Water is then added to the residue and the latter is extracted with chloroform. The chloroform extract is dried over sodium sulfate, concentrated under vacuum, and the residue is fractionated with an oil pump. The product, ω-(4-ketopyridyl-1)-n-hexane, passes over at 210° C. During cooling, the distillate solidifies to a crystalline mass having a melting point of 45° C.

EXAMPLE 5

ω-(2-Ketopyridyl-1)-n-octadecane 28.9 g. of 1-chloroctadecane and 9.5 g. of pyridone-2 potassium salt are heated for about 2 hours under reflux in a solution of 2.6 g. of Na in 150 ml. of ethanol and thereafter concentrated under vacuum. The residue is mixed with water under agitation and extracted with chloroform. After drying over sodium sulfate, the chloroform is distilled off and the residue fractionated by means of an oil pump. The product, ω-(2-ketopyridyl-1)-n-octadecane, passes over at between 224° and 226° C.

Yield: 27 g., about 78% of theory.

EXAMPLE 6

4-(2-Ketopyridyl-1)-2,2-dimethylbutane

This compound is synthesized by treating pyridone-2 potassium salt with 3,3-dimethylbutyl chloride analogously as in Example 1. The substance is distilled with an oil pump at 152° C.

EXAMPLE 7

ω-(2,4-Diketo-3-methyl-6-chloropyrimidyl-1)-n-hexane

This product is prepared as described in Example 1 by treating the potassium salt of 2,4-diketo-3-methyl-6- chloropyrimidine in acetone with 1-bromohexane. The obtained ω-(2,4-diketo-3-methyl-6-chloropyrimidyl-1')-n-hexane has a melting point of 52° C.

Yield: almost quantitative

EXAMPLE 8

ω-(2'-Ketopyridyl-1')-n-hexanol-1

13.3 g. of pyridone-2 potassium is heated under reflux with 13.7 g. of 6-chlorohexanol-1 in 20 ml. of ethanol for up to 4 hours. The thus-formed potassium chloride is filtered off, the filtrate is concentrated, and it is then fractionated under vacuum by means of an oil pump. The product, ω-(2'-ketopyridyl-1')-n-hexanol-1, passes over at 180°–182° C.

Yield: 80% of theory

The compound is soluble in water as well as in chloroform.

In accordance with the above-described method, it is furthermore possible to produce the following compounds:

1. ω-(4'-Ketopyridyl-1')-n-butanol-1
2. ω-(2'-Thiopyridyl-1')-n-octanol-1
3. ω-(3'-Methyl-2',4'-diketo-6'-chloropyrimidyl-1')-n-hexanol-1
4. ω-(2'-Ketopyridyl-5'-chloro-1')-n-octadecanol-1 by the use of the corresponding alkali metal salts and by utilizing, for example, the following compounds, respectively, as the starting haloalkanols:

1. 4-Bromobutanol-1
2. 8-Chloroctanol-1
3. 6-Chlorohexanol-1
4. ω-Chloroctadecanol-1.

Accordingly, the above ω-substituted-1-alkanols are prepared by reacting, for example, the appropriate alkali metal salt of the starting heterocyclic compound such as γ-pyridone with the corresponding haloalkanol such as 4-bromobutanol-1 under the same conditions as noted, for instance, in Example 1.

The compound of the invention are novel and possess the useful pharmaceutical property mentioned hereinabove.

The invention being thus described, it will be obvious that the same may be varied in many ways. Such variations are not to be regarded as a departure from the spirit and scope of the invention, and all such modifications are intended to be included within the scope of the following claims.

I claim:

1. A compound selected from the group consisting of ω-(2'-ketopyridyl-1')-n-hexanol-1; ω-(2'-thiopyridyl-1')-n-octanol-1; and ω-(2'-ketopyridyl-5'-chloro-1')-n-octadecanol-1.

2. The compound ω-(2'-ketopyridyl-1')-n-hexanol-1.

UNITED STATES PATENT AND TRADEMARK OFFICE
CERTIFICATE OF CORRECTION

PATENT NO. : 4,067,877
DATED : January 10, 1978
INVENTOR(S) : Kailash Kumar GAURI It is certified that error appears in the above-identified patent and that said Letters Patent are hereby corrected as shown below:

IN THE HEADING OF THE PATENT ADD THE FOLLOWING:

--[30] FOREIGN APPLICATION PRIORITY DATA

June 9, 1972 Germany P22 28 289.9--

Signed and Sealed this

Twentieth Day of June 1978

[SEAL]

Attest:

RUTH C. MASON
Attesting Officer

DONALD W. BANNER
Commissioner of Patents and Trademarks